US006844195B2

(12) United States Patent
Craine (10) Patent No.: US 6,844,195 B2
(45) Date of Patent: Jan. 18, 2005

(54) METHOD FOR DETERMINING LOCATION OF GASTROINTESTINAL BLEEDING

(75) Inventor: Brian L. Craine, Fairfax, CA (US)

(73) Assignee: Western Research Company, Tucson, AZ (US)

(*) Notice: Subject to any disclaimer, the term of this patent is extended or adjusted under 35 U.S.C. 154(b) by 219 days.

(21) Appl. No.: 09/994,143

(22) Filed: Nov. 26, 2001

(65) Prior Publication Data

US 2002/0076820 A1 Jun. 20, 2002

Related U.S. Application Data

(60) Provisional application No. 60/250,493, filed on Dec. 1, 2000.

(51) Int. Cl.[7] .............................................. G01N 33/72
(52) U.S. Cl. .............................. 436/66; 436/63; 436/64; 436/67; 436/164
(58) Field of Search .............................. 436/66, 63, 64, 436/67, 164

(56) References Cited

U.S. PATENT DOCUMENTS

| | | | | |
|---|---|---|---|---|
| 4,347,311 A | * | 8/1982 | Schmitz ........................ | 435/5 |
| 4,853,338 A | * | 8/1989 | Benezra et al. ............... | 436/66 |
| 5,008,388 A | * | 4/1991 | Ingberg et al. ............. | 540/145 |
| 5,064,766 A | | 11/1991 | Wardlaw et al. ............... | 436/66 |
| 5,460,969 A | * | 10/1995 | Fielder et al. ................. | 436/66 |
| 5,759,866 A | * | 6/1998 | Machida et al. ............. | 436/518 |

OTHER PUBLICATIONS

Hacker "Detection of occult bleeding in the gastrointestinal tract with special reference to the appearance of coproatoporphyrin and hemoglobin", Arch. Verdauungs–Krankh. (1935), 58, 268–97 , Abstract.*

Brady et al. The oxygenated coplexes of the two catalyticaly active oxidation–reduction states of L–tryptophan–2,3–oxidation–reduction states of L–tryptophan–2,3–dioxygenase JBC , 1975, v. 250, issue 13, pp. 5041–5048, Abstract.*
HYDROPFLUORtm–Combo, http://www.sdix.com/PDF/Products/hydrflurpkg.pdf, bibliography 1985–1986.*
"Spectrophotometric determination of hermoglobin redox states summary", http://www.biochem.wisc.edu/biochem651/Experiments/04SPY/Manual/027SPY.pdf, May 2000.*
"Interpretation of Diagnostic Tests" by Jacques Wallach, A Synopsis of Laboratory Medicine, Little, Brown and Company, p. 154.
"Performance Characteristics and Comparison of Two Immunochemical and Two Guaiac Fecal Occult Blood Screening Tests for Colorectal Neoplasis" by Paul Rozen, Judith Knaani, and Ziona Samuel, Digestive Diseases and Sciences, vol. 42, No. 10 (Oct. 1997), pp. 2064–2071.
"Measurement of Degraded Fecal Hemoglobin–Heme to Estimate Gastrointestinal Site of Occult Bleeding" by Goldschmiedt et al, Digestive Diseases and Sciences, vol. 33, No. 5 (May 1988), pp. 605–608.

(List continued on next page.)

Primary Examiner—Yelena G. Gakh
(74) Attorney, Agent, or Firm—Cahill, von Hellens & Glazer P.L.C.

(57) ABSTRACT

A method for determining if blood in a stool sample originated from the upper or lower gastrointestinal tract. This includes a method for purifying and concentrating hemoglobin and its products from a stool sample to allow a simple and sensitive spectrophotometric analysis. A rapid, noninvasive determination of whether the blood originated from an upper gastrointestinal or lower gastrointestinal site is made on the basis of changes in the absorption spectra of hemoglobin that occur when hemoglobin is exposed to a highly acidic environment.

29 Claims, 4 Drawing Sheets

OTHER PUBLICATIONS

"Fecal Blood Levels in Health and Disease" by Ahlquist et al., the New England Journal of Medicine, vol. 312, No. 22, May 30, 1985, pp. 1422–1428.

"Immunochemical Dectection of Human Blood in Feces" by Barrows et al., A.J.C.P. vol. 69, No. 3, Mar. 1978, pp. 342–346.

"The 'HemoQuant' Test: A Specific and Quantiative Determination of Home (Hemoglobin) in Feces and Other Materials" by Schwartz et al., Clinical Chemistry, vol. 29, No. 12, 1983, pp. 2061–2067.

"Screening For Colorectal Cancer" by Ransohoff and Lang, The New England Journal of Medicine, vol. 325, No. 1, Jul. 4, 1991, pp. 37–41.

* cited by examiner

METHOD FOR DETERMINING LOCATION OF GASTROINTESTINAL BLEEDING

CROSS REFERENCE TO RELATED APPLICATION

This application claims the benefit of prior filed now abandoned U.S. provisional application Ser. No. 60/250,493, filed Dec. 1, 2000 entitled "METHOD FOR LOCALIZING THE SITE OF GASTROINTESTINAL BLEEDING" by Brian L. Craine.

BACKGROUND OF THE INVENTION

This invention relates to a way of determining whether bleeding in the gastrointestinal tract originates in the upper gastrointestinal tract or the lower gastrointestinal tract.

Gastrointestinal bleeding is a common clinical problem with many and varied causes. Gross bleeding into the GI tract is responsible for about two percent of all emergency medical hospitalizations in the United States. Of these approximately 85,000 patients per year, the majority have upper GI bleeding from peptic or gastric ulcers. On the other end of the spectrum are patients with occult GI bleeding. Occult GI bleeding is loss of blood into the digestive tract that is not apparent to the patient or to the physician by physical examination. Studies of healthy subjects between ages 40 and 50 have shown that about 3–6% of individuals have occult blood loss. See Rozen P, Knaani J, Samuel Z, "Comparison of two immunochemical and two guaiac fecal occult blood screening tests for colorectal neoplasia", Digestive Diseases and Sciences, 1997. 42(10):2064–71. These statistics clearly show the enormous number of patients that have blood loss in the GI tract as an important medical sign.

Whether the bleeding is an acute and significant blood loss or is a slow occult bleed, the first diagnostic question to be considered is the location of the source of bleeding. The clinician attempts to define the bleeding as an "upper GI bleed" or a "lower GI bleed". This is the key assessment that determines the sequence of patient management. The decision to perform an upper GI endoscopy or lower GI endoscopy, the type of radiographic studies to perform, and the medications that may be prescribed all hinge on the foregoing assessment of the bleeding location.

Many patients that experience a gross, acute bleeding episode are rather easily categorized with respect to the bleeding site according to their clinical history and naso-gastric aspiration (which for example may return blood from the stomach). However, even for acute bleeding, the source of bleeding is not always immediately ascertainable. As many as 10% of duodenal ulcer bleeds have negative naso-gastric aspirations in the emergency room, possibly due to edema or pyloric spasm. Melena in the stool (resulting from bacterial degradation of the blood) can be seen in both upper and lower GI bleeding and may lead to confusion as to the location of the bleeding source. Therefore, even in patients with acute blood loss, a means of distinguishing upper from lower bleeding sites at the point of patient care would represent a useful and needed capability in about 10–15% of the cases.

In contrast, for patients with occult GI bleeding, the source of bleeding is never ascertained by clinical history. The causes of occult GI bleeding are similar to those of clinically apparent bleeding. The majority, about 60–70%, are upper GI bleeds due to peptic/gastric ulcers or erosive gastritis. Gastric ulcers are much more prevalent now than 15 years ago due to the increased use of nonsteroidal anti-inflammatory drugs.

However, the most important application of testing for occult GI bleeding is to detect lower GI bleeding as a screen for colorectal neoplasia. For example, the American Cancer Society recommends that everyone over the age of 50 undergo annual fecal occult blood testing. These screening practices produce a large number of patients with positive occult blood who must then be further evaluated. This generally involves the patient undergoing a colonoscopy exam (with an average cost of about $1,000 per work-up). It has been estimated by the Congressional Budget Office that this screening costs Medicare over $100 million per year. To fully implement this screening for colorectal cancer for all Americans over the age of 50 would cost about $1.2 billion dollars per year. See Ransohoff D F, Lang C A. Screening for colorectal cancer. N. Engl. J. Med.,1991. 325:37. This expensive work-up could be avoided for the majority of patients having an upper GI bleeding source if it were possible to reliably determine that their bleeding is indeed an upper GI bleeding before performing a colonoscopy.

The unavailability of any simple laboratory test to classify GI bleeding as an upper or lower GI bleed is a problem that is well-understood by nearly all clinicians. It is not surprising then that while evaluating a new and highly sensitive fluorometric test (HemoQuant™) for occult blood, the need for such a test prompted Schwartz et al to publish an article suggesting further study of the HemoQuant™ test as a possible means of distinguishing bleeding sites. See Schwartz S, Dahl J, Ellefson M, Ahlquist D., "The Hemo-Quant test: A specific and quantitative determination of heme (hemoglobin) in feces and other materials", Clin. Chem. 1985:29:2061–2067. The HemoQuant™ test involves the conversion of heme into dicarboxylic porphyrins (e.g. hematoporphyrin). Heme is a core, non-protein part of hemoglobin that binds iron, and provides much of the material which is visible to spectroscopy. The dicarboxylic porphyrins absorb strongly at 402 nanometers and fluoresce at 653 nanometers. This provides a quantitative and sensitive measure of the hemoglobin present. As discussed above, hemoglobin in the intestines is exposed to a large population of bacteria, which can also degrade hemoglobin to dicarboxylic porphyrins. These products may be measured separately and are called the intestinal converted fraction (ICF). It was postulated that the more proximal the bleeding site the longer the exposure to bacteria and the greater the ICF. Indeed, this was subsequently noted to be the general trend. See Ahlquist D A, McGill D B, Schwartz S, Taylor S F, et al., "Fecal blood levels in health and disease: A study using HemoQuant", N. Engl. J. Med. 1985. 312:1422–1428. However, after studying a large sample of patients it was found that while the ICF appeared to be affected by the site and amount of bleeding (for example the mean ICF was significantly lower in patients with bleeding from sigmoid or rectal lesions compared to more proximal lesions) it was concluded that the considerable individual differences in enteric heme metabolism severely compromised the predictive value of the ICF. See Goldschmidt M D, Ahlquist D A, Wieand H S, McGill D B, et. al., "Measurement of degraded fecal hemoglobin-heme to estimate gastrointestinal site of occult bleeding: appraisal of its clinical utility", Digestive Diseases and Sciences, 1988, 33:605–608. Consequently, the ICF was thought to be of no clinical utilitly in estimating the bleeding site.

An alternative approach is described in U.S. Pat. No. 5,064,766, entitled "Method for differentiating the source of occult gastrointestinal bleeding", issued Nov. 12, 1991 to Wardlaw and Levine. This patent describes the collection of a stool sample on a charged absorbent medium, such as silica, for the purposes of separating hematin and hemoglobin through a process of chromatography. This can be accomplished since the charge on these molecules is different. The location of the hematin and hemoglobin molecules are then visualized by using a guaic color reaction. Thus the relative concentration of the different molecules can be determined. Hematin is a degradation product of hemoglobin that is promoted by exposure to acid in the stomach and the action of bacteria in the lower gastrointestinal tract. The premise is that large amounts of hematin would indicate that the blood originated from the upper gastrointestinal tract. However, bacterial action in the gastrointestinal tract is highly variable with unpredictable amounts of hematin formed, which greatly reduces the specificity of the test. Perhaps for this reason the foregoing method has not seen any practical use.

Therefore, nearly ten years after the development of the closest prior art, there still is no available effective practical test to aid in this critical diagnostic determination.

Thus, there is an unmet need for a technique that economically, rapidly, and reliably indicates whether gastrointestinal bleeding originates in the upper gastrointestinal tract or lower gastrointestinal tract of a patient.

SUMMARY OF THE INVENTION

Accordingly, it is an object of the present invention to provide a rapid and economical test for estimating the location of gastrointestinal bleeding in a patient that requires only a few minutes to perform in an ordinary examining room setting.

It is another object of the invention to provide a reliable and economical test for estimating the location of gastrointestinal bleeding in a patient.

It is another object of the invention to provide a test for estimating the location of gastrointestinal bleeding in a patient which avoids inaccuracy due to large variations in enteric heme metabolism of hemoglobin-related molecules in various patients.

It is another object of the invention to provide a test for estimating the location of gastrointestinal bleeding in patients which avoids inaccuracy due to large variation in bacterial action in the gastrointestinal tract on formation of hematin in various patients.

It is another object of the invention to provide a reliable, rapid, and economical test for estimating the location of gastrointestinal bleeding in a patient that avoids the shortcomings of the above prior art.

It is another object of the invention to provide a reliable, rapid, and economical non-invasive test for estimating location of gastrointestinal bleeding in a patient.

It is another object of the invention to provide a reliable, rapid, and economical test for determining if gastrointestinal bleeding detected in a patient has a significant risk of being associated with colon cancer.

Briefly described, and in accordance with one embodiment thereof, the invention provides a means for determining with a high degree of certainty whether blood in a patients' stool originated from a bleeding site in the duodenum or above or a bleeding site in the colon or small intestine. A stool specimen from a patient that has been determined to be bleeding in the gastrointestinal tract is placed directly into a tube containing a hypotonic buffer. The stool specimen is delivered to a doctor (or other health-care professional) who centrifuges the specimen to remove particulate matter. A portion of the supernatant is then filtered through a small nitrocellulose filter. In the described embodiment, the filter is then wetted with a 60% glycerol buffer solution, which increases the translucency of the filter. The filter is then placed in a spectrophotometer, which determines an absorbance curve for the filter relative to a blank filter that does not have a specimen on it. The absorbance curve is analyzed by a computer program to determine whether the bleeding is from the upper or lower gastrointestinal tract, on the basis of the relative amounts of ferric and ferrous heme present in the sample, and the computer displays information indicating whether the bleeding is from the upper or lower gastrointestinal tract. A sample with significant amounts of ferric heme would be considered to represent a likely upper gastrointestinal bleed. A sample with significant amounts of ferroheme would be considered a probable lower gastrointestinal bleed. The physician would then tailor the treatment of the patient with this information. For example, if the test indicates an upper GI bleed, the physician may give the patient a trial with an H2 blocker and follow the patient's progress, saving $1,000 of resource utilization (i.e. colonoscopy procedure and work-up). If the test indicates a lower GI bleed, then the patient would need to be further evaluated, for example by colonoscopy, because of the risk of colorectal cancer.

DETAILED DESCRIPTION OF THE PREFERRED EMBODIMENTS

The present invention is based on the fact that the spectral properties of the heme portion of hemoglobin which has passed through the acidic environment of the human stomach are different from the spectral properties of the heme portion of hemoglobin that has passed only through the lower digestive tract. In particular, the stomach excretes hydrochloric acid, which results in an acidic environment that is isotonic with a pH of about 1. This is a unique chemical environment, with essentially all other regions of the body having a pH close to 7.4. As the stomach contents are passed out of the stomach, they are rapidly neutralized to become isotonic, and have a neutral pH. The large intestine absorbs water and electrolytes as it produces a solid stool that is about 70% water, isotonic, with a neutral pH. A major component of the solid material is bacteria. The major pigment in stool is urobilinogen, which is a product of systemic hemoglobin degradation.

Bleeding directly into the GI tract may occur at many sites, from nosebleeds to hemorrhoids, with common sites in between such as stomach ulcers and intestinal polyps. Depending upon the location of bleeding, the blood cells will be exposed to the chemical environments described above and will therefore have a different chemical exposure history. Specifically, bleeding from the duodenum, referred to as an "upper GI bleed", and above will be exposed to an isotonic acidic environment. Bleeding from below the duodenum, referred to as a "lower GI bleed", will be exposed to an isotonic, neutral pH environment. Blood in the GI tract, particularly from upper GI bleeds, is subject to the action of digestive proteases in the stomach and proximal small intestine. This protease activity can release the heme moiety (e.g., the heme portion) from the hemoglobin. However, even in upper GI bleeds about 50% of patients have immunologically intact hemoglobin in their stools. See Barrows G H, Burton R M, Jarret M T, et al., "Immunochemical Detection of Human Blood in feces", 1978. 69:342–346. The heme moiety can be re-adsorbed in the proximal small intestine but only to a small degree. (That is, some of the hemoglobin passes through the upper and lower gastrointestinal tracts without much degradation.) Both types of bleeding will be exposed to bacteria and bacterial degradation, although perhaps to a somewhat greater degree for the upper GI bleeding sites. This bacterial degradation involves conversion of the iron heme to hematoporphyrins (through the loss of iron and vinyl side groups) and generally occurs to about 20% of the heme present in a GI bleed of greater than 20 mls per day.

The exposure to the extreme acidic conditions of a person's stomach are, however, a most unique event which will effect the oxidation state of the iron in the heme moiety converting the normal ferroheme to ferriheme. However, action in the lower gastrointestinal tract does not result in a conversion from ferroheme to ferriheme, which enhances the specificity of this phenomena. In accordance with the present invention, the above mentioned conversion provides a means to distinguish between the locations of bleeding sources. To distinguish between an upper GI bleed and a lower GI bleed, it should be noted that the main chromophore of hemoglobin is iron heme (or iron protoporphyrin). Iron heme has a spectrum characterized by a main Soret band (around 415 nanometers) and two additional visible bands: the α band (at about 576 nanometers) and the β band (at about 540 nanometers). The visible spectrum of this molecule is affected by the binding of oxygen, the oxidation state of the chelated iron, the loss of the iron, and modifications to the side groups and solvent conditions (notably pH).

Figure 1:
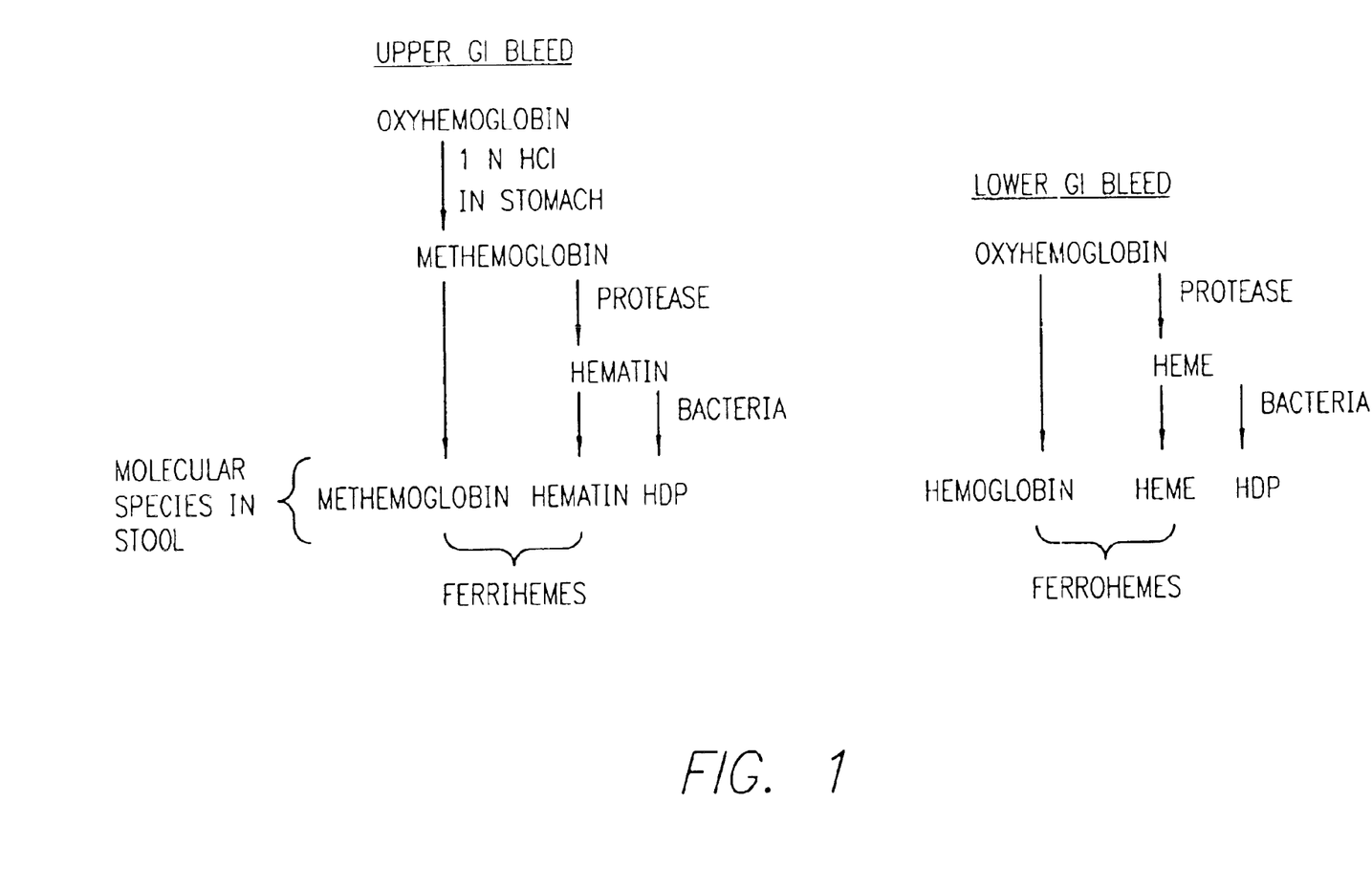
FIG. 1 is a diagram that is useful in explaining modifications of hemoglobin and derivatives during intraluminal bleeding from either the upper GI tract or lower GI tract.

The changes that occur to the iron heme molecule in the GI tract are illustrated in FIG. 1, wherein HDP is hematoporphyrin. In accordance with the present invention, it is recognized that the critical difference between an upper and lower GI bleed is that the upper GI bleed should result in the presence of ferriheme, while the lower GI bleed should result in ferroheme. Thus, the stomach provides a unique chemical environment to which the blood from an upper GI bleed is exposed. The very low pH, isotonic solution in the stomach results in a characteristic change in the spectral properties of heme, which is the result of the conversion of the chelated iron from the ferrous to ferric state.

Figure 2:
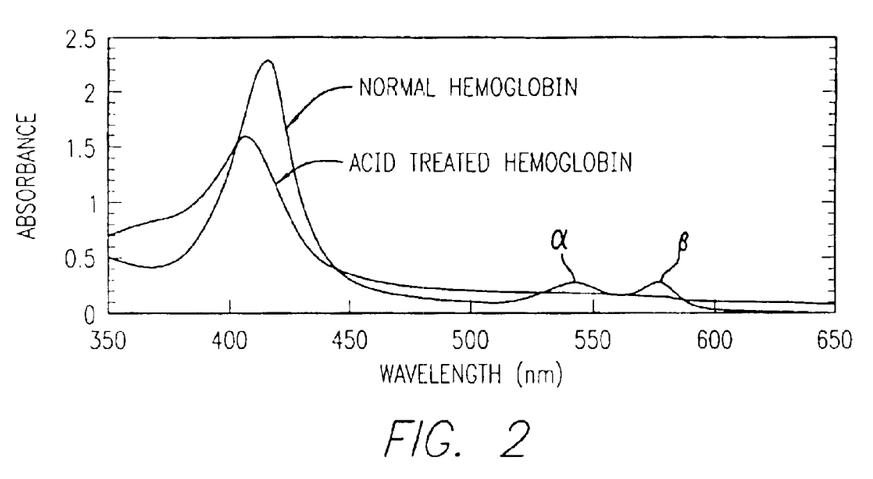
FIG. 2 is a graph that is useful in explaining visible spectra of (1) hemoglobin (HB, ferroheme) obtained from normal red blood cells, and (2) cells exposed to a pH 1, isotonic solution (acid HB, ferriheme) for 1 minute.

These changes that occur to hemoglobin molecules that have originated from an upper GI bleed and therefore have passed through the acidic environment of the stomach are indicated by the absorption characteristic shown in FIG. 2. Specifically, the two main absorption peaks labeled α and β around 540 nanometers and 576 nanometers, respectively, for "normal hemoglobin" molecules are eliminated from "acid-treated hemoglobin" molecules that have passed through the stomach. Also, there is a shift in the absorption peak of the main Soret band (from about 415 nanometers to 408 nanometers) between the absorption characteristic of normal hemoglobin molecules and "acid treated" hemoglobin molecules. There is also a reduction in the molar extinction coefficient for the Soret band. The absorption pattern is due to the heme component, as digestion with trypsin or proteinase K (as might occur in the GI tract) does not significantly alter the absorption spectra.

In accordance with the present invention, these significant changes provide the basis of an effective method to distinguish between an upper and lower source of GI bleeding.

In order to take practical advantage of these spectral changes it is necessary to (1) prevent degradation of the stool sample, (2) concentrate the hemoglobin (and related heme products) for sensitive detection, and (3) purify the hemoglobin (and related heme products) to allow for the identification of the relevant species.

With these requirements in mind, a simple sample preparation protocol has been developed in accordance with the present invention that allows for the foregoing steps (1)–(3). Basically, and as subsequently described in more detail, a small amount of fecal material (e.g. 40 mg) is mixed in a small tube with 1 milliliter of a hypotonic buffer (Tris [Hydroxymethyl]aminomethane 0.01M, 0.001 M Ethylenediaminetetraacetic acid 0.001M adjusted to pH 7.4). This hypotonic solution liberates hemoglobin and heme-containing products. The aqueous portion is filtered onto a nitrocellulose membrane filter, which effectively and selectively concentrates hemoglobin and derivatives from the fecal supernatant (satisfying the above requirements of steps (2) and (3). The translucency of nitrocellulose filter is then increased (i.e., the nitrocellulose filter is made more transparent) by adding a 60% glycerol in TE buffer, and then the absorption spectra can be read directly from the membrane.

Figure 3:
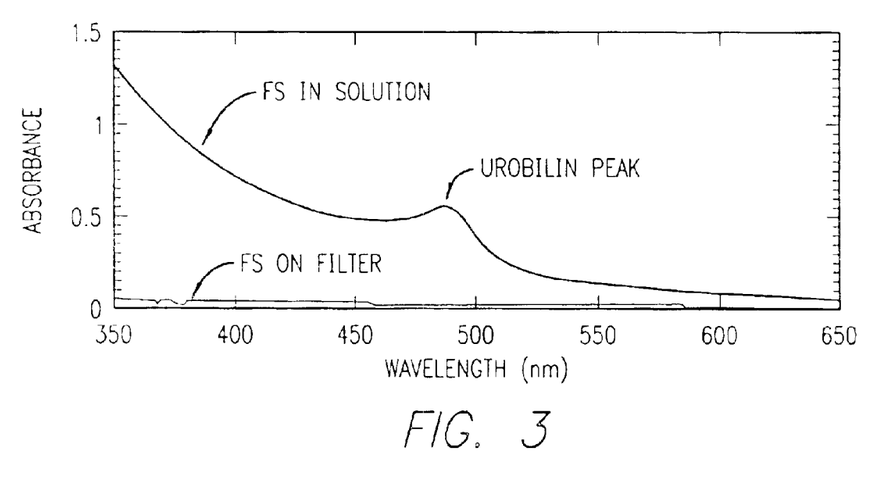
FIG. 3 is a graph that illustrates absorption spectra of fecal supernatant (FS) in solution and immobilized.

The benefits of this approach can be appreciated by comparing the absorption characteristic curves for the fecal supernatant in solution and after concentration on the filter. The fecal supernatant (FS) from the aqueous extract of fecal material has an absorption spectra characterized by an exponential increase in absorption toward the blue end of the spectra and a single major peak with a peak maxima at 488 nanometers as shown in FIG. 3. This single peak is urobilin, which is the main fecal pigment. Filtering a FS sample from a guaic negative sample shows that very little of the material normally present in the FS is bound to the translucent membrane. This should have the effect of reducing the background absorbance in the region of the main Soret band, making it easier to characterize the heme components in the FS; see FIG. 4.

The ability of this technique to detect hemoglobin in the stool can be tested by mixing a small amount of blood (2 $\mu$l) with a stool sample (40 mg). It should be noted that the normal level of blood loss is about 0.5 $\mu$l of blood per 40 mg stool, while a level of about 7 µl of blood per 40 mg stool is considered to be a positive occult bleed. See Wallach J. "Interpretation of Diagnostic Tests", Little, Brown and Company (Boston). 1992. p. 154. The sample was extracted and the spectrum of the supernatant before and after binding to the translucent membrane is compared in FIG. 4. This result shows the expected benefit in signal to background noise that can be obtained. In fact, the hemoglobin absorption peaks in curves A and B at 540 and 576 nanometers, respectively, can be clearly detected in the membrane bound sample, but are completely obscured in solution. These peaks are important in producing a high specificity test.

The present invention provides (1) a non-invasive technique for evaluating blood in the stool to determine whether the blood originates from an upper or lower gastrointestinal source, which technique includes (2) providing a rapid and simple means to purify hemoglobin and related molecules from a stool sample allowing for a sensitive and meaningful spectral analysis to be performed, and (3) a simple means to increase the translucency of nitrocellulose filters to aid in the spectral analysis of hemoglobin and related products from stool samples.

Figure 4:
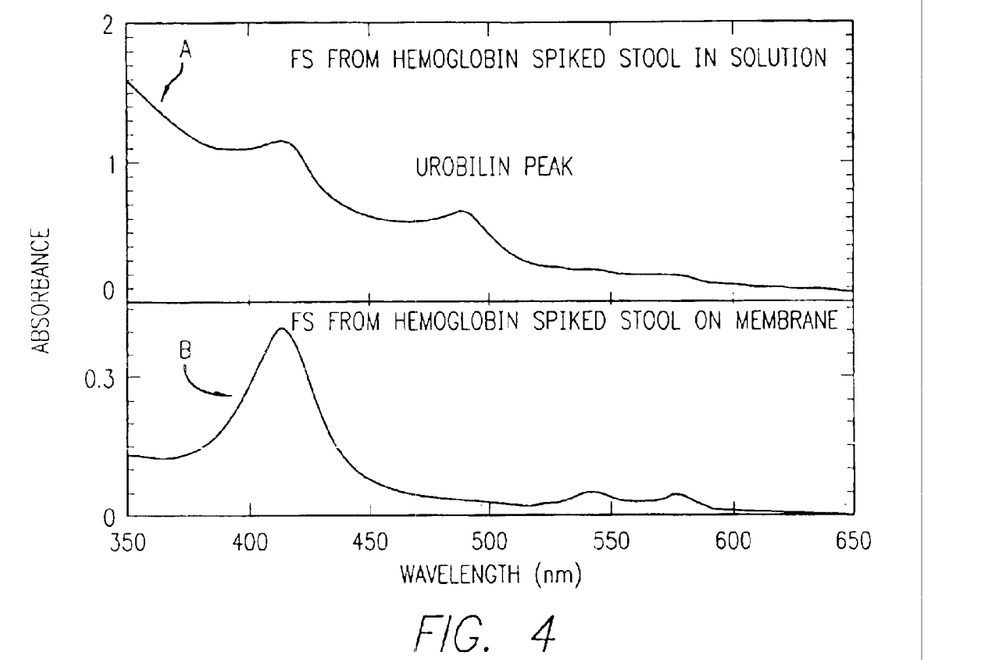
FIG. 4 is a graph that illustrates absorption spectra of hemoglobin isolated from fecal material (1) in solution and (2) on a translucent membrane, for normal stool sample that was spiked with 2 $\mu$l of blood prior to extraction to simulate a lower GI bleed.
Figure 5:
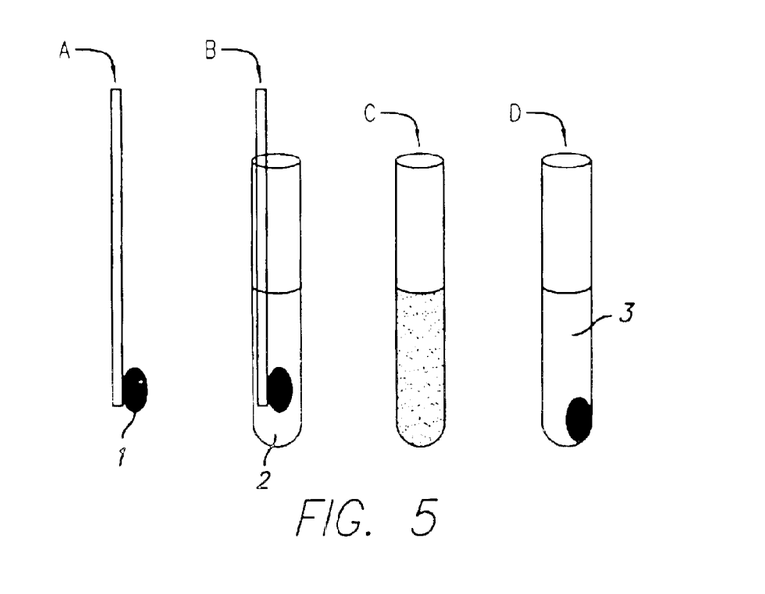
FIG. 5 is a diagram useful in explaining the preparation of a fecal extract by centrifugation of a stool sample mixed in a sample buffer.

The preparation of the stool sample for the spectral analysis required to provide the above described absorption characteristic of FIGS. 2–4 is described next, with reference to FIGS. 5, 6A and 6B. In the preferred embodiment, the classification of a gastrointestinal bleed as an upper GI bleed or a lower GI bleed is accomplished through the analysis of a small stool sample. In FIG. 5, "A" indicates the collection of the stool sample 1 on a collection stick, and "B" indicates the mixing of the stool sample 1 in a sample TE buffer solution 2. A diagrammatic representation of the stool sample 1 mixed with and suspended in sample TE buffer 2 is represented by "C". Reference character "D" diagrammatically indicates the sample tube after centrifugation with the particulate matter collected at the bottom of the tube, the fecal extract 3 being the solution above that particulate matter. It is to be understood that once the suspended particulate matter is separated from the liquid, either by centrifuging or by filtering through subsequently described particulate filter 10, the resulting liquid is referred to as the "fecal extract", and the fecal extract with no particulate matter is what is then passed through the sample nitrocellulose filter 6. Particulate matter would interfere with the spectroscopy performed on the fecal extract.

The 40 milligram stool sample 1 is collected on the collection stick during a traditional digital rectal examination by the physician or by the patient at home. The stool sample is placed immediately (before drying) into a test tube and mixed with one milliliter of an aqueous, hypotonic TE buffer 2 (Tris[Hydroxymethyl]aminomethane 0.01M, Ethylenediaminetetraacetic acid 0.001M, adjusted to pH 7.4). The blood cells in the stool sample suspended in the sample TE buffer swell and lyse in the hypotonic buffer, releasing hemoglobin into the TE buffer, as indicated by "C" in FIG. 5. The Ethylenediaminetetraacetic acid (EDTA) acts as a preservative stabilizing the hemoglobin and related molecules by preventing or greatly slowing the degradation process that would normally occur.

The mixture of the stool sample and the TE buffer then can be centrifuged in a clinical centrifuge at top speed for three minutes. The centrifugation results in the separation of an aqueous fecal extract 3 and particulate matter to the bottom of the tube, as shown by "D" in FIG. 5. Alternatively, instead of centrifuging, the aqueous fecal extract 3 indicated by "C" in FIG. 5 can be passed through a particulate barrier filter 10 in sample filter cup 4 as shown in FIG. 6C.

Figure 6A:
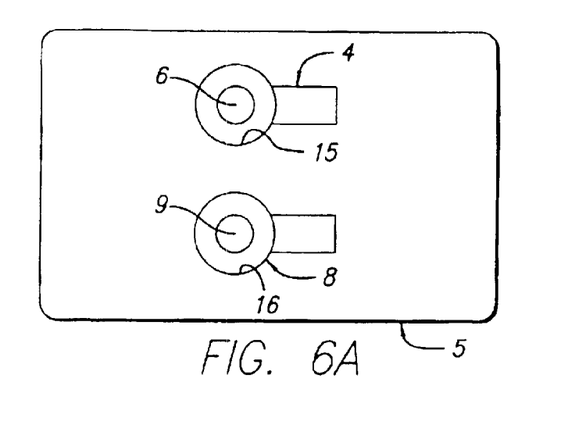
FIG. 6A is a top view diagram useful in explaining the use of a sample cassette in performing the method of the present invention.
Figure 6B:
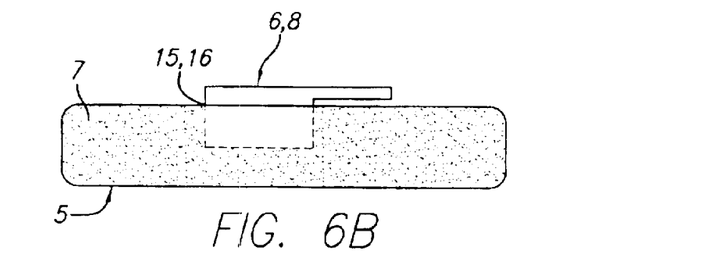
FIG. 6B is a side view diagram of the sample cassette of FIG. 6A.
Figure 6C:
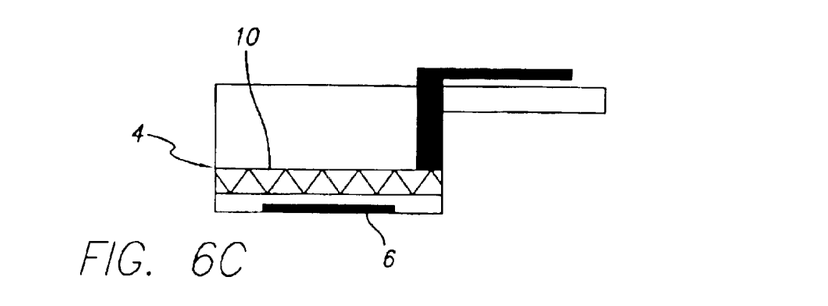
FIG. 6C is a side view diagram illustrating the sample cup 4 of FIG. 6A with a sample nitrocellulose filter, with and without a particulate barrier therein.
Figure 6D:
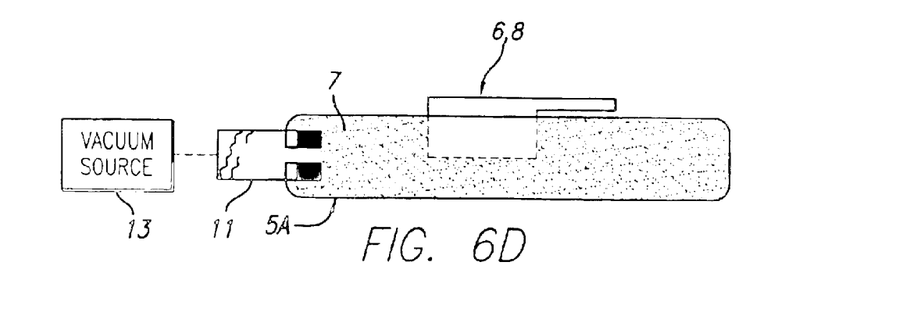
FIG. 6D is a side view diagram as shown in FIG. 6B further including a fitting for receiving a vacuum.

Referring to FIGS. 6A through 6C, one-tenth milliliter of the fecal extract is placed in an open-bottom sample filter cup 4 of sample cassette 5 having its open bottom covered by an attached $3/16^{th}$ inch diameter piece of nitrocellulose filter 6. This results in the fecal supernatant being filtered by capillary action through the nitrocellulose filter 6. Absorbent paper 7 within the body of a cassette 5 speeds up the filtering process because it draws liquid by capillary action through the nitrocellulose filters in the bottoms of the of filter cups 4 and 8. (Note that the capillary action can be assisted by providing a partial vacuum within cassette 5. This is illustrated in FIG. 6D, wherein a conventional Leur lock fitting 11 is provided on the side of cassette 5A for connection to a vacuum source 13. Vacuum source 13 can be a syringe.)

The sample filter cup 4 is removed from cassette 5 and fifteen microliters of clarifying buffer, for example, a buffer consisting of 60% glycerol in the TE buffer, is added to wet the attached nitrocellulose filter 6 to make it more translucent. A reference filter cup 8 is removed from the cassette and fifteen microliters of the clarifying buffer is added to the reference filter cup, which wets an attached nitrocellulose filter 9 to make it more translucent. The sample buffer can be any one of a number of aqueous hypotonic buffers that includes TE buffer comprised of 0.01M Tris [Hydroxymethyl]aminomethane, 0.001 M Ethylenediaminetetraacetic acid adjusted to pH 7.4.

The reference filter cup 8 is placed into a visible spectrophotometer and the transmission of the light from the light source through the nitrocellulose filter 9 is adjusted to provide a maximum reading that is still in the measurable range. The reference filter cup 8 is then removed from the spectrophotometer and replaced with the sample filter cup 4. The characteristic of the transmission of light through nitrocellulose filter 6 is then determined and compared to that of the nitrocellulose filter 9 which determines the sample absorbance spectrum of the material bound to and hence concentrated on the nitrocellulose filter 6 over the wavelength ranges of 400 to 600 nanometers, as shown by curve B in FIG. 4. The sample absorbance spectrum is analyzed by means of an artificial neural net, such as Neuroshell Classifier®, available from Ward Systems Group, Inc., Frederick, Md. the main character), running on a conventional personal computer. The neural net, which has been trained with multiple spectra of normal and acid-treated hemoglobin mixed with stool samples, classifies the sample spectrum as a result of either upper gastrointestinal bleeding, lower gastrointestinal bleeding or no blood present.

The amount of ferriheme and ferroheme present in the fecal extract can be determined by various other spectroscopy methods, including infra-red spectroscopy, and Fourier transform infra-red spectroscopy (FTIR). The sample spectra are obtained from ranges of light wavelengths including infra-red wavelengths and a small number of discrete wavelengths.

Alternatively, the mathematical analysis of the sample absorption spectra can be accomplished by various algorithms, including Gaussian Jordan elimination algorithms, singular value decomposition algorithms, or Simplex method algorithms.

In the well-known Simplex method, the mathematical analysis of the sample absorption spectra can be implemented on a microcomputer and using coefficients obtained from standard spectra for ferrohemoglobin, ferrihemoglobin, urobilinogen and fecal supernatant to maximize the function $$z = \in_{1,\lambda 420} x_1 + \in_{2,\lambda 420} x_2 + \in_{3,\lambda 420} x_3 + \in_{4,\lambda 420} x_4,$$

where $\in$ is the absorption coefficient for the indicated component (1–4) at the indicated wavelength ($\lambda$) obtained from the standard spectra, and x is the number of units of the indicated component (where component 1 is ferrohemes, component 2 is ferrihemes, component 3 is fecal supernatant, and component 4 is urobilinogen) and subject to the following constraining equations:

$$A_{\lambda 412}/\in_{2,\lambda 412} = \in_{1,\lambda 412} x_1 + \in_{2,\lambda 412} x_2$$

$$0 \geq x_4 - x_3$$

$$A_{\lambda 412} = \in_{1,\lambda 412} x_1 + \in_{2,\lambda 412} x_2 + \in_{3,\lambda 412} x_3 + \in_{4,\lambda 412} x_4$$

$$A_{\lambda 440} = \in_{1,\lambda 440} x_1 + \in_{2,\lambda 440} x_2 + \in_{3,\lambda 440} x_3 + \in_{4,\lambda 440} x_4$$

$$A_{\lambda 494} = \in_{1,\lambda 494} x_1 + \in_{2,\lambda 494} x_2 + \in_{3,\lambda 494} x_3 + \in_{4,\lambda 494} x_4$$

$$A_{\lambda 475} = \in_{1,\lambda 475} x_1 + \in_{2,\lambda 475} x_2 + \in_{3,\lambda 475} x_3 + \in_{4,\lambda 475} x_4$$

$$A_{\lambda 559} = \in_{1,\lambda 559} x_1 + \in_{2,\lambda 559} x_2 + \in_{3,\lambda 559} x_3 + \in_{4,\lambda 559} x_4$$

$$A_{\lambda 578} = \in_{1,\lambda 578} x_1 + \in_{2,\lambda 578} x_2 + \in_{3,\lambda 578} x_3 + \in_{4,\lambda 578} x_4,$$

where A is the absorption value at the indicated wavelength ($\lambda$) of the sample absorption.

The physician may view the sample spectrum on the computer screen to verify the diagnosis provided by the neural net. The physician would then commence with the indicated management of the bleeding condition.

The above described methods of the present invention can be used to provide a means to determine in a practical fashion whether blood in the stool originated from bleeding in or into the upper or lower gastrointestinal tract. This inexpensive and non-invasive spectral analysis of hemoglobin related molecules isolated from stool samples provides healthcare workers, for the first time, a practical test for immediately identifying the location of bleeding in the gastrointestinal tract. Furthermore, this invention has the additional advantage that it may be easily employed during a routine exam at the site of patient contact. The above methods are easily integrated into the current patient examination routines, are compatible with equipment used by various physicians, and are non-invasive and easy to implement. Furthermore, the sensitivity and specificity of the above methods are sufficient to minimize false positive and false negative results, and the time between the examination of the patient and the availability of the results is relatively minimal.

The sensitivity of the above described technique can be increased by increasing the volume of the fecal extract passed through the nitrocellulose sample filter. This may be important for determining whether blood present in the stool sample came from the upper or lower gastrointestinal tract in cases wherein the amount of blood present in the stool sample is very small, because some relevant cancers cause only very minute amounts of bleeding.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention.

For example, a variety of other methods to prepare the hemoglobin and related molecules for spectral analysis could be employed. The hemoglobin and hemoglobin products in the stool sample may be purified by various affinity binding, phase separation, hydrophobic interaction, or antibody selection methods. In some cases, it may be possible to use reflection spectroscopy directly from stool sample, without the above described purification procedures, to characterize the heme. Other materials than nitrocellulose can be used in place of the nitrocellulose filter disclosed herein. For example, DEAE filters (ie., Diethylaminoethyl filters) might be used. The reference nitrocellulose filter 9 does not necessarily have to be supported in reference cup 8, as long as reference nitrocellulose filter 9 is treated in essentially the same manner as sample filter 6 except that no fecal extract comes in contact with reference nitrocellulose filter 9. The reference nitrocellulose filter 9 instead could be supported by any suitable support device while it is being wetted by the same liquid buffer used to wet the sample filter 4 to make it transparent, in which case the additional opening 16 could be omitted from cassette 5. Other sample buffer solutions than one described could be used, for example phosphate buffer solutions.

What is claimed is:

1. A method for determining whether blood in a stool came from an upper gastrointestinal site or a lower gastrointestinal site, comprising the steps of:

(a) collecting a stool sample containing hemoglobin and/or iron heme compounds derived from hemoglobin in its ferrous state and/or its ferric state and preparing the stool sample at a predetermined pH for analysis by spectroscopy;

(b) measuring an absorption spectrum of the stool sample at the predetermined pH using a spectrophotometer calibrated relative to a first absorption spectrum with a first Soret absorption peak approximately centered at a first wavelength of about 415 nanometers for pure ferrous heme at the predetermined pH and a second absorption spectrum with a second Soret absorption peak approximately centered at a second wavelength of about 408 nanometers for pure ferric heme at the predetermined pH; and (c) determining whether the blood in the stool came from the upper gastrointestinal site or the lower gastrointestinal site based on an analysis of the stool sample absorption spectrum by determining that the blood in the stool sample has passed through stomach acid and therefore came from the upper gastrointestinal tract if an absorption peak of a main Soret band of the stool sample absorption spectrum is closer to the second wavelength of about 408 nanometers than to the first wavelength of about 415 nanometers, or that the blood in the stool sample has not passed through stomach acid and therefore came from the lower gastrointestinal tract if an absorption peak of the Soret band of the stool sample absorption spectra is closer to the first wavelength of about 415 nanometers than to the second wavelength of about 408 nanometers.

2. The method of claim 1 wherein step (a) includes placing the stool sample into a sample tube containing a liquid buffer to create a sample stool suspension;

separating the sample stool suspension into a particulate matter portion and a liquid portion to create a fecal extract; and filtering an amount of the fecal extract through a sample filter causing hemoglobin and related molecules present in the fecal extract to adhere to the sample filter; and wherein step (d) includes measuring the sample absorption spectrum from hemoglobin and related molecules which adhere to the sample nitrocellulose filter.

3. The method of claim 2 wherein the filtering step includes
filtering the amount of the fecal extract through a sample nitrocellulose filter causing hemoglobin and related molecules present in the fecal extract to adhere to the sample nitrocellulose filter.

4. The method of claim 3 wherein the sample nitrocellulose filter and the reference nitrocellulose are wetted with a 60% glycerol by volume sample buffer to increase the translucency of the nitrocellulose sample filter aiding in the acquisition of the sample absorption spectra.

5. The method of claim 2 wherein the liquid buffer belongs to a group of aqueous hypotonic buffers that includes TE buffer comprised of 0.01M Tris [Hydroxymethyl]aminometbane, 0.001 M Ethylenediaminetetraacetic acid adjusted to pH 7.4.

6. The method of claim 2 wherein the stool particulate matter is separated from the liquid phase by centrifugation and the resulting supernatant fraction becomes the fecal extract.

7. The method of claim 2 wherein the stool particulate matter is separated from the liquid portion using a sample cassette, where the stool suspension is passed through a removable particulate barrier allowing the fecal extract to pass through the sample nitrocellulose filter and deposit the hemoglobin and related molecules onto the sample nitrocellulose filter.

8. The method of claim 2 wherein a mathematical analysis of the sample absorption spectra is accomplished by use of a trained artificial neural network running on a computing device.

9. The method of claim 2 wherein a mathematical analysis of the sample absorption spectra is performed by means of a Simplex method implemented on a processor and using coefficients obtained from standard spectra ferrohemoglobin, ferrihemoglobin, urobilinoglobin and fecal supernatant to maximize the function:

$$z = \in_{1,\lambda 420} x_1 + \in_{2,\lambda 420} x_2 + \in_{3,\lambda 420} x_3 + \in_{4,\lambda 420} x_4$$

where $\in$ is the absorption coefficient for the indicated component (1–4) at the indicated wavelength ($\lambda$) obtained from the standard spectra, and x is the number of units of the indicated component (where component 1 is ferrohemes, component 2 is ferrihemes, component 3 is fecal supernatant, and component 4 is urobilinogen) and subject to the following constraining equations:

$$A_{\lambda 412} / \in_{2,\lambda 412} = \in_{1,\lambda 412} x_1 + \in_{2,\lambda 12} x_2$$

$$0 \geq x_4 - x_3$$

$$A_{\lambda 412} = \in_{1,\lambda 412} x_1 + \in_{2,\lambda 412} x_2 + \in_{3,\lambda 412} x_3 + \in_{4,\lambda 412} x_4$$

$$A_{\lambda 440} = \in_{1,\lambda 440} x_1 + \in_{2,\lambda 440} x_2 + \in_{3,\lambda 440} x_3 + \in_{4,\lambda 440} x_4$$

$$A_{\lambda 494} = \in_{1,\lambda 494} x_1 + \in_{2,\lambda 494} x_2 + \in_{3,\lambda 494} x_3 + \in_{4,\lambda 494} x_4$$

$$A_{\lambda 475} = \in_{1,\lambda 475} x_1 + \in_{2,\lambda 475} x_2 + \in_{3,\lambda 475} x_3 + \in_{4,\lambda 475} x_4$$

$$A_{\lambda 559} = \in_{1,\lambda 559} x_1 + \in_{2,\lambda 559} x_2 + \in_{3,\lambda 559} x_3 + \in_{4,\lambda 559} x_4$$

$$A_{\lambda 578} = \in_{1,\lambda 578} x_1 + \in_{2,\lambda 578} x_2 + \in_{3,\lambda 578} x_3 + \in_{4,\lambda 578} x_4,$$

where A is the absorption value at the indicated wavelength ($\lambda$) of the sample absorption spectra.

10. The method of claim 2 wherein a mathematical analysis of the sample absorption spectra is according to a Gaussian Jordan elimination algorithm, a singular value decomposition algorithm, or an artificial neural network algorithm.

11. The method of claim 1 wherein step (d) is performed by visual inspection of the sample absorption spectra.

12. The method of claim 1 including purifying hemoglobin and hemoglobin products in the stool sample by means of one of an affinity binding method, a phase separation method, a hydrophobic interaction method, and an antibody selection method.

13. The method of claim 1 wherein the sample absorption spectrum is obtained over the range of 400 to 600 nanometers.

14. The method of claim 1 wherein the predetermined pH is equal to approximately 7.4.

15. The method of claim 1 wherein the predetermined pH is an approximately neutral pH.

16. A method for determining whether blood in a stool came from a lower gastrointestinal site, comprising the steps of:
(a) collecting a stool sample containing hemoglobin and/or iron heme compounds derived from hemoglobin in its ferrous state and/or its ferric state and preparing the stool sample at a predetermined pH for analysis by spectroscopy;
(b) measuring an absorption spectrum of the stool sample at the predetermined pH using a spectrophotometer calibrated relative to an absorption spectrum for pure ferrous heme at the predetermined pH having a Soret absorption peak approximately centered at a wavelength of about 415 nanometers, an $\alpha$ secondary absorption peak approximately centered at a wavelength of about 540 nanometers, and a $\beta$ secondary absorption peak approximately centered at a wavelength of about 576 nanometers, and
(c) determining if the blood in the stool came from the lower gastrointestinal site based on an analysis of the stool sample absorption spectrum by determining that the blood in the stool sample has not passed through stomach acid and therefore came from the lower gastrointestinal tract if the stool sample absorption spectrum includes an $\alpha$ secondary absorption peak having a wavelength of about 540 nanometers and a $\beta$ secondary absorption peak having a wavelength of about 576 nanometers.

17. The method of claim 16 wherein the predetermined pH is equal to approximately 7.4.

18. The method of claim 16 wherein the predetermined pH is an approximately neutral pH.

19. A method for determining whether blood in a stool came from an upper gastrointestinal site or a lower gastrointestinal site, comprising the steps of:
(a) collecting a stool sample containing hemoglobin and/or iron heme compounds derived from hemoglobin in its ferrous state and/or its ferric state and preparing the stool sample at a predetermined pH for analysis by spectroscopy;
(b) measuring an absorption spectrum of the stool sample at the predetermined pH using a spectrophotometer calibrated relative to a first absorption spectrum with a first Soret absorption peak approximately centered at a first wavelength of about 415 nanometers for pure ferrous heme at the predetermined pH and a second absorption spectrum with a second Soret absorption peak approximately centered at a second wavelength of about 408 nanometers for pure ferric heme at the predetermined pH, the first absorption spectrum having an $\alpha$ secondary absorption peak approximately centered at a wavelength of about 540 nanometers and a $\beta$ secondary absorption peak approximately centered at a wavelength of about 576 nanometers; and (c) determining whether the blood in the stool came from the upper gastrointestinal site or the lower gastrointestinal site based on an analysis of the stool sample absorption spectrum by determining that the blood in the stool sample came from the lower gastrointestinal tract if an absorption peak of a main Soret band of the stool sample absorption spectrum is closer to the first wavelength of about 415 nanometers than to the second wavelength of about 408 nanometers and the stool sample absorption spectrum includes a first secondary absorption peak having a wavelength of about 540 nanometers and a second secondary absorption peak having a wavelength of about 576 nanometers, or by determining that the blood in the stool sample came from the upper gastrointestinal tract if an absorption peak of a main Soret band of the stool sample absorption spectrum is closer to the second wavelength of about 408 nanometers than to the first wavelength of about 415 nanometers and the first and second secondary absorption peaks are not present.

20. The method of claim 19 wherein the predetermined pH is equal to approximately 7.4.

21. The method of claim 19 wherein the predetermined pH is an approximately neutral pH.

22. A method for determining whether blood in a stool came from an upper gastrointestinal site or a lower gastrointestinal site, comprising the steps of:

(a) collecting a stool sample containing hemoglobin and/or iron heme compounds derived from hemoglobin in its ferrous state and/or its ferric state and preparing the stool sample at a predetermined pH for analysis by spectroscopy;

(b) measuring an absorption spectrum of the stool sample at the predetermined pH using a spectrophotometer calibrated relative to a first absorption spectrum for pure ferrous heme at the predetermined pH and a second absorption spectrum for pure ferric heme at the predetermined pH; and (c) determining whether the blood in the stool came from the upper gastrointestinal site or the lower gastrointestinal site based on an analysis of the stool sample absorption spectrum by determining that the blood in the stool sample has passed through stomach acid and therefore came from the upper gastrointestinal tract if the stool sample absorption spectrum is closer to the second absorption spectrum than to the first absorption spectrum, or that the blood in the stool sample has not passed through stomach acid and therefore came from the lower gastrointestinal tract if the stool sample absorption spectra is closer to the first absorption spectrum than to the second absorption spectrum.

23. The method of claim 22 wherein step (c) includes performing the analysis to determine if an absorption peak of a main Soret band of the first absorption spectrum is closer to approximately 408 nanometers than to 415 nanometers, and determining that the blood in the stool sample came from the upper gastrointestinal tract if the main Soret band is closer to 408 nanometers.

24. The method of claim 22 wherein step (c) includes performing the analysis to determine if α and β secondary absorption peaks of the stool sample absorption spectrum are present at approximately 540 nanometers and 576 nanometers, and determining that the blood in the stool sample came from the lower gastrointestinal tract if the absorption peaks are present.

25. The method of claim 22 wherein step (c) includes classifying the type of gastrointestinal bleed based on a mathematical analysis of the stool sample absorption spectrum.

26. The method of claim 25 including performing the mathematical analysis of the stool sample absorption spectrum by means of a trained artificial neural network running on a computing device.

27. The method of claim 25 wherein the mathematical analysis of the sample absorption spectra is performed by means of a Simplex method implemented on a processor and using coefficients obtained from standard spectra for ferrohemoglobin, ferrihemoglobin, urobilinogen and fecal supernatant to maximize the function:

$$z = \in_{1,\lambda 420} x_1 + \in_{2,\lambda 1420} x_2 + \in_{3,\lambda 420} x_3 + \in_{4,\lambda 420} x_4$$

where $\in$ is the absorption coefficient for the indicated component (1–4) at the indicated wavelength ($\lambda$) obtained from the standard spectra, and x is the number of units of the indicated component (where component 1 is ferrohemes, component 2 is ferrihemes, component 3 is fecal supernatant, and component 4 is urobilinogen) and subject to the following constraining equations:

$$A_{\lambda 412}/\in_{2,\lambda 412} = \in_{1,\lambda 412} x_1 + \in_{2,\lambda 12} x_2$$

$$0 \geq x_4 - x_3$$

$$A_{\lambda 412} = \in_{1,\lambda 412} x_1 + \in_{2,\lambda 412} x_2 + \in_{3,\lambda 412} x_3 + \in_{4,\lambda 412} x_4$$

$$A_{\lambda 440} = \in_{1,\lambda 440} x_1 + \in_{2,\lambda 440} x_2 + \in_{3,\lambda 440} x_3 + \in_{4,\lambda 440} x_4$$

$$A_{\lambda 494} = \in_{1,\lambda 494} x_1 + \in_{2,\lambda 494} x_2 + \in_{3,\lambda 494} x_3 + \in_{4,\lambda 494} x_4$$

$$A_{\lambda 475} = \in_{1,\lambda 475} x_1 + \in_{2,\lambda 475} x_2 + \in_{3,\lambda 475} x_3 + \in_{4,\lambda 475} x_4$$

$$A_{\lambda 559} = \in_{1,\lambda 559} x_1 + \in_{2,\lambda 559} x_2 + \in_{3,\lambda 559} x_3 + \in_{4,\lambda 559} x_4$$

$$A_{\lambda 578} = \in_{1,\lambda 578} x_1 + \in_{2,\lambda 578} x_2 + \in_{3,\lambda 578} x_3 + \in_{4,\lambda 578} x_4,$$

where A is the absorption value at the indicated wavelength ($\lambda$) of the sample absorption spectra.

28. The method of claim 22 including purifying hemoglobin and hemoglobin products in the stool sample by means of one of an affinity binding method, a phase separation method, a hydrophobic interaction method, and an antibody selection method.

29. The method of claim 22 wherein the stool sample absorption spectrum is obtained over the range of 400 to 600 nanometers.

* * * * *